United States Patent
Kiani (10) Patent No.: US 8,998,809 B2
(45) Date of Patent: Apr. 7, 2015

(54) SYSTEMS AND METHODS FOR CALIBRATING MINIMALLY INVASIVE AND NON-INVASIVE PHYSIOLOGICAL SENSOR DEVICES

(75) Inventor: Massi E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 1903 days.

(21) Appl. No.: 11/746,451

(22) Filed: May 9, 2007

(65) Prior Publication Data

US 2007/0265514 A1 Nov. 15, 2007

Related U.S. Application Data

(60) Provisional application No. 60/800,512, filed on May 15, 2006.

(51) Int. Cl.
| | |
|---|---|
| A61B 5/05 | (2006.01) |
| G01N 33/66 | (2006.01) |
| A61B 5/145 | (2006.01) |
| A61B 5/1495 | (2006.01) |
| G06F 19/00 | (2011.01) |
| A61B 5/1459 | (2006.01) |
| A61B 5/00 | (2006.01) |

(52) U.S. Cl.
CPC ............ *G01N 33/66* (2013.01); *A61B 5/14542* (2013.01); *A61B 5/1495* (2013.01); *G06F 19/3412* (2013.01); *A61B 5/14532* (2013.01); *A61B 5/1459* (2013.01); *A61B 5/7275* (2013.01); *A61B 2560/0223* (2013.01); *A61B 2562/0295* (2013.01); *G06F 19/3468* (2013.01)

(58) Field of Classification Search
USPC ........... 600/345–347, 365; 435/4, 14; 422/50, 422/420–429; 204/403.01–403.15; 702/23; 604/64–66

See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |

(Continued)

FOREIGN PATENT DOCUMENTS

WO WO 2012/075322 6/2012

OTHER PUBLICATIONS

Smith, "The Pursuit of Noninvasive Glucose: Hunting the Deceitful Turkey", Retrieved from http://www.mendosa.com/noninvasive_glucose.pdf (retrieved on Jan. 3, 2013) pp. i-129 (2006).

(Continued)

*Primary Examiner* — Michael D'Angelo
(74) *Attorney, Agent, or Firm* — Knobbe Martens Olson & Bear LLP (57) ABSTRACT

A calibration system is disclosed for calibrating a first physiological monitoring device using a second physiological monitoring device. The first physiological monitor measures a first indication of a physiological parameter. The second physiological monitor measures a second indication of the physiological parameter. The first and second indications are used to calibrate the first physiological monitoring device.

7 Claims, 8 Drawing Sheets

(56) References Cited

U.S. PATENT DOCUMENTS

| | | |
|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,505,828 A * | 4/1996 | Wong et al. ............... 205/777.5 |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,522,903 B1 * | 2/2003 | Berman et al. ............... 600/316 |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Pishney et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |

(56) References Cited

U.S. PATENT DOCUMENTS

| | | |
|---|---|---|
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 2003/0130616 A1* | 7/2003 | Steil et al. ............ 604/66 |
| 2005/0203360 A1 | 9/2005 | Brauker et al. |
| 2006/0020192 A1* | 1/2006 | Brister et al. ............ 600/345 |
| 2006/0229531 A1 | 10/2006 | Goldberger et al. |
| 2007/0265514 A1 | 11/2007 | Kiani |
| 2010/0099964 A1 | 4/2010 | O'Reilly et al. |
| 2010/0168537 A1 | 7/2010 | Ueda et al. |

OTHER PUBLICATIONS

International Search Report and Written Opinion issued in application No. PCT/US2012/060074 on Jan. 11, 2013.

* cited by examiner

SYSTEMS AND METHODS FOR CALIBRATING MINIMALLY INVASIVE AND NON-INVASIVE PHYSIOLOGICAL SENSOR DEVICES

PRIORITY CLAIM TO RELATED PROVISIONAL APPLICATIONS

The present application claims priority benefit under 35 U.S.C. § 119(e) to U.S. Provisional Patent Application Ser. No. 60/800,512, filed May 15, 2006, entitled "SYSTEMS AND METHODS FOR CALIBRATING MINIMALLY INVASIVE AND NON-INVASIVE PHYSIOLOGICAL SENSOR DEVICES." The present application incorporates the foregoing disclosures herein by reference.

FIELD OF THE INVENTION

The present invention relates to the field of patient monitor calibration. More specifically, the present invention relates to using a first physiological monitor to calibrate a second physiological monitor.

BACKGROUND

Diabetes is a common cause of kidney disease, blindness among adults under the age of 65, and limb amputation. The effects of diabetes can be greatly reduced, if not eliminated all together, with proper monitoring of blood glucose. Many glucose monitors in use today require that a person be pricked with a sharp object in order to draw a small amount of blood to test for glucose levels. This process of measuring blood is often painful and uncomfortable. Although minimally and non-invasive blood glucose systems are being developed, they generally suffer from signal processing challenges affecting accuracy. One common challenge of minimally invasive glucose monitoring systems is referred to as drift. Drift generally occurs during the first few hours or days that a minimally invasive monitor's probe is inserted in the body and may cause inaccuracies.

SUMMARY

Figure 1:
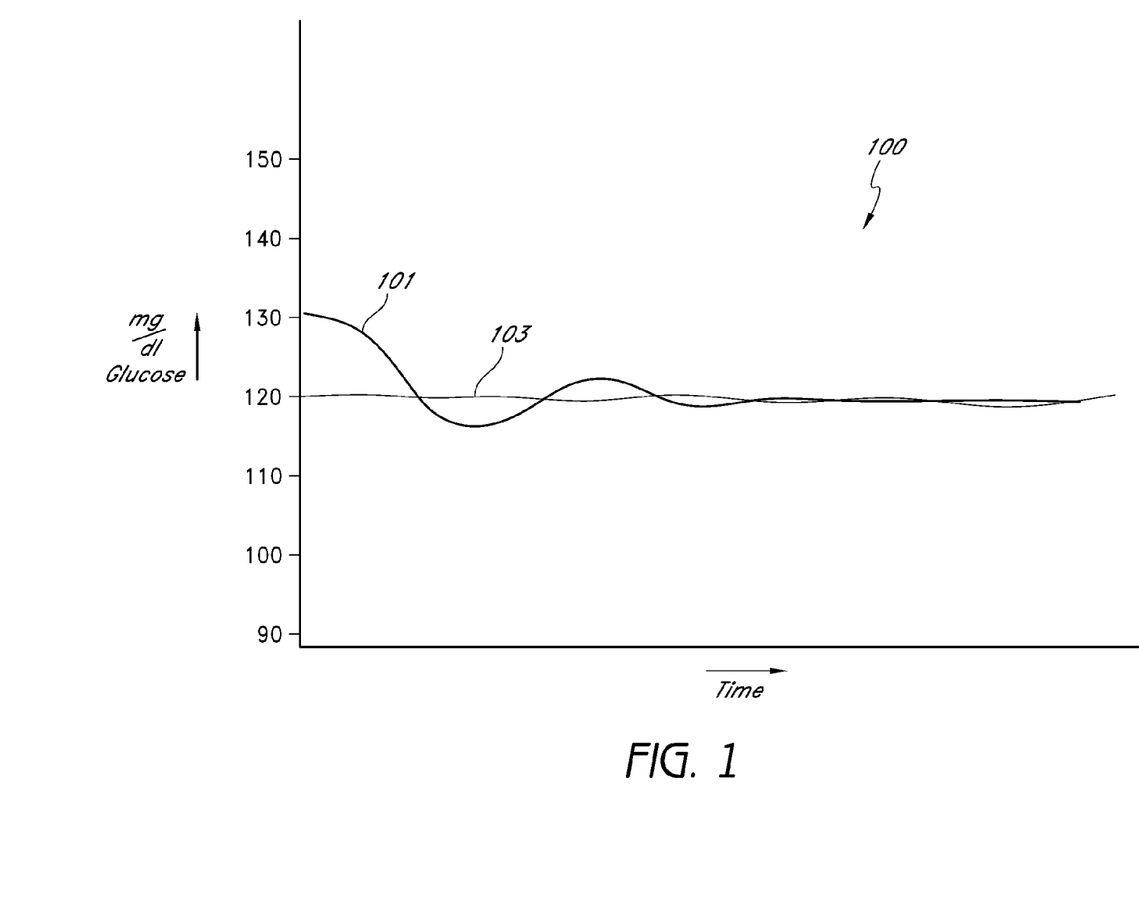
FIG. 1 illustrates a graph of actual glucose v. measured glucose for a glucose monitor experiencing drift.

Aspects of the present disclosure include systems and methods for calibrating minimally invasive and non-invasive physiological sensor devices. The calibration is used to improve accuracy. In some embodiments, when the system begins taking measurements, the system may experience drift. FIG. 1 illustrates a graph 100 of glucose levels 101 in a patient vs. measured glucose 103 measured by a minimally invasive glucose monitor affected by drift. As illustrated, for a period of time, referred to herein as the calibration period, the measured glucose is less accurate due to, for example, drift. In minimally invasive systems, drift may be caused by protein buildup on the implanted device. In other systems, drift or other inaccuracies may be caused by any number of other issues known to an artisan from the disclosure herein. As with all patient monitors, more accurate and more reliable systems are preferred.

In an embodiment, a minimally invasive glucose monitor is described. The minimally invasive glucose monitor includes a probe which is inserted into a patient. The probe nearly continuously measures the patient's glucose levels and reports glucose information to the minimally invasive glucose monitor. The minimally invasive glucose monitor also includes a calibration input for receiving glucose information about the patient derived from a reliable glucose monitor. The glucose information received from the reliable glucose monitor is used to calibrate the minimally invasive glucose monitor. The minimally invasive glucose monitor may also include one or more outputs for outputting glucose and calibration related information. The inputs and outputs can be wired or wireless.

Although described with respect to glucose monitoring, a person of skill in the art will recognize that the present calibration system can be used to monitor and calibrate other physiological parameters, such as, for example, blood oxygen levels, blood carbon monoxide levels, blood pH levels, methemoglobin levels, pulse rates, trend or physiological traces, or any other physiological parameter. In addition, although described with respect to a minimally invasive patient monitor, the present disclosure is also applicable to the calibration of both invasive and non-invasive patient monitors.

In an embodiment, a method of calibrating a glucose measurement device is disclosed. The method includes acquiring a first indication of a glucose measurement from a first device, acquiring a second indication of a glucose measurement from a second device, and calibrating the second device using the first indication from the first device and the second indication from the second device. In an embodiment, the first and second devices comprise patient monitors. In an embodiment, the first and second devices are operably connected to the same patient. In an embodiment, the first and second indications are obtained at substantially the same time. In an embodiment, calibration comprises one or more of modeling, scaling, transforming, finding a best fit, finding a linear fit, filtering, adaptive correlation, and cross correlation. In an embodiment, the first device comprises an invasive physiological measurement device. In an embodiment, the second device comprises a minimally invasive physiological measurement device. In an embodiment, the second device comprises a non invasive physiological measurement device.

In an embodiment, a method of calibrating a physiological measurement device is disclosed. The method includes acquiring a first indication of one or more physiological measurements from a first device, acquiring a second indication of the one or more physiological measurements from a second device, and calibrating the second device using the first indication from the first device and the second indication from the second device. In an embodiment, the first and second devices comprise patient monitors. In an embodiment, the first and second devices are operably connected to the same patient. In an embodiment, the first and second indications are obtained at substantially the same time. In an embodiment, calibration comprises one or more of modeling, scaling, transforming, finding a best fit, finding a linear fit, filtering, adaptive correlation, and cross correlation. In an embodiment, the one or more physiological parameters comprise one or more of glucose, blood oxygen, pH, blood carbon monoxide levels, and methemoglobin. In an embodiment, the first device comprises an invasive physiological measurement device. In an embodiment, the second device comprises a minimally invasive physiological measurement device. In an embodiment, the second device comprises a non invasive physiological measurement device.

In an embodiment, a calibration system for calibrating a physiological measurement monitor is disclosed. The calibration system includes a first physiological monitor, a calibration module including a first input for inputting measured physiological data and a second input for inputting reliable data indicative of one or more physiological parameters. The calibration module is configured to calibrate the first physiological monitor using the information inputted over the first and second inputs. In an embodiment, the calibration system also includes a second physiological monitor for measuring the reliable data indicative of one or more physiological parameters. In an embodiment, the second physiological monitor comprises an invasive physiological measurement device. In an embodiment, the first physiological monitor comprises a minimally invasive physiological measurement device. In an embodiment, the first physiological monitor comprises a non invasive physiological measurement device. In an embodiment, the calibration system also includes one or more signal outputs. In an embodiment, the one or more signal outputs comprise a display output. In an embodiment, the one or more signal outputs comprise a trend output. In an embodiment, the one or more signal outputs comprise a waveform output. In an embodiment, the waveform output comprises a synthesized waveform. In an embodiment, the waveform output comprises a scaled waveform. In an embodiment, the one or more signal outputs comprise an error output.

In an embodiment, a method of calibrating a physiological measurement device is disclosed. The method of calibrating a physiological measurement includes acquiring a first indication of a glucose measurement from a first device, acquiring a second indication of a glucose measurement from a second device, and comparing the first indication and the second indication. Based on the comparison of the first indication and the second indication, if the first and second indications are not the same or close, the method also includes calibrating the second device using the first indication from the first device and the second indication from the second device, waiting an amount of time and requiring the first and second indications, comparing the reacquired first and second indications, and based on the comparison of the reacquired first and second indications, recalibrating the second device using the reacquired first and second indications.

In an embodiment, the amount of time comprises a predetermined amount of time. In an embodiment, the amount of time comprises about 5 minutes or less to about 12 hours or more. In an embodiment, the predetermined amount of time comprises about 5 minutes to about 10 minutes. In an embodiment, the predetermined amount of time comprises about 1 hour to about 2 hours. In an embodiment, the method also includes dynamically determining the amount of time. In an embodiment, dynamically determining comprises determining an amount of time based on the comparison of the first and second indications. In an embodiment, dynamically determining comprises determining an amount of time based on the comparison of the reacquired first and second indications.

BRIEF DESCRIPTION OF THE DRAWINGS

The drawings and the associated descriptions are provided to illustrate embodiments of the disclosure and not to limit the scope of the claims.

DETAILED DESCRIPTION

Embodiments of the present disclosure include systems and methods for calibrating a physiological monitoring device. A reliable, often invasive, method of measuring a physiological parameter is used to calibrate measurements of a minimally invasive or non-invasive physiological measurement device. In an embodiment, the reliable monitor and the minimally invasive or non-invasive monitor measure the same physiological parameter from the same patient within a time period deemed appropriate. In an embodiment, a patient can be set up with a long term, minimally invasive physiological measurement device with minimized discomfort during the initialization period. In an embodiment, a patient can use a minimally invasive physiological measurement device to continuously measure a physiological parameter, using an invasive measurement device periodically to calibrate the minimally invasive physiological measurement device. In an embodiment, the physiological parameter is one or more of glucose, blood oxygen, pH, blood carbon monoxide levels, and methemoglobin.

Figure 2:
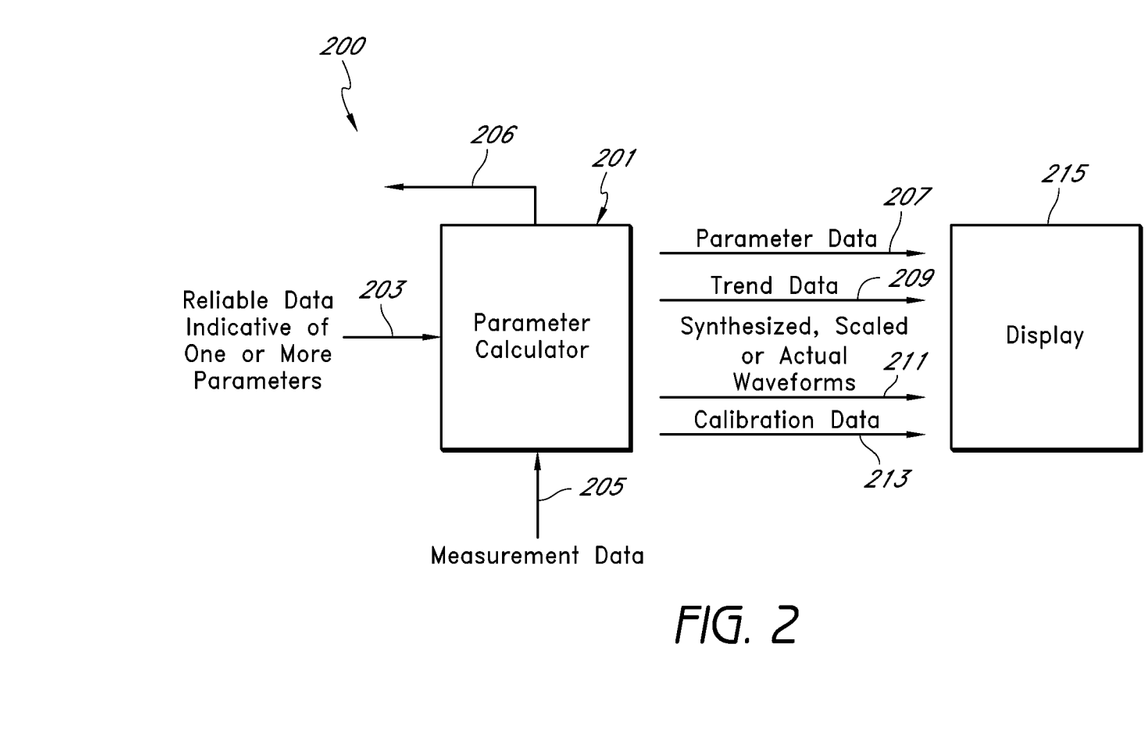
FIG. 2 illustrates a calibration system.

FIG. 2 illustrates a calibration system 200. The calibration system includes a parameter calculator 201. The parameter calculator includes one or more inputs 203 for reliable data indicative of one or more parameters and one or more inputs 205 for measurement data. The reliable data indicative of one or more parameters is communicated from a reliable, often invasive, patient monitor. The measurement data is communicated from a physiological sensor.

The parameter calculator 201 uses the reliable data indicative of one or more parameters to calibrate, if necessary, the measurement data or information derived from the measurement data. Calibration may include modeling, scaling, transforming, finding a best fit, finding a linear fit, filtering, adaptive correlation, cross correlation, or any other calibration steps known to a skilled artisan from the disclosure herein.

The parameter calculator 201 can calculate one or more physiological parameters and output information indicative of that parameter. The parameter calculator 201 may also advantageously calculate trend data and synthesize or scale waveform data. The parameter calculator 201 includes one or more outputs, such as, for example, parameter data output 207, trend data output 209, synthesized, scaled, or actual waveform output 211, or calibration data output 213. The parameter data output 207 communicates data indicative of one or more physiological measurements. The trend data output 209 communicates data indicative of trend information for the one or more physiological measurements. The synthesized, scaled, or actual waveform data output 211 communications waveform data which has been synthesized, scaled, or unaltered. The calibration data output 213 communicates information related to calibrations performed by the parameter calculator 201. The outputs 207, 209, 211, 213 can communicate with display 215, a separate patient monitoring device, or other device configured to receiving physiological parameter information.

In an embodiment, the parameter calculator 201 is included within a single device. In an embodiment, the parameter calculator 201 is included within several separate devices. In an embodiment, the parameter calculator 201 comprises a processor, processor board, or OEM board. In an embodiment, the parameter calculator 201 is portable. In an embodiment, the parameter calculator 201 comprises a desktop parameter calculator. Data communicated between the various components of the calibration system can be communicated through cables or wirelessly. A skilled artisan will also understand from the disclosure herein, that other inputs and/or outputs can be included with the system of the present disclosure. For example, an error data output can be used to communicate the error calculated between the measured data and the reliable data.

Figure 3:
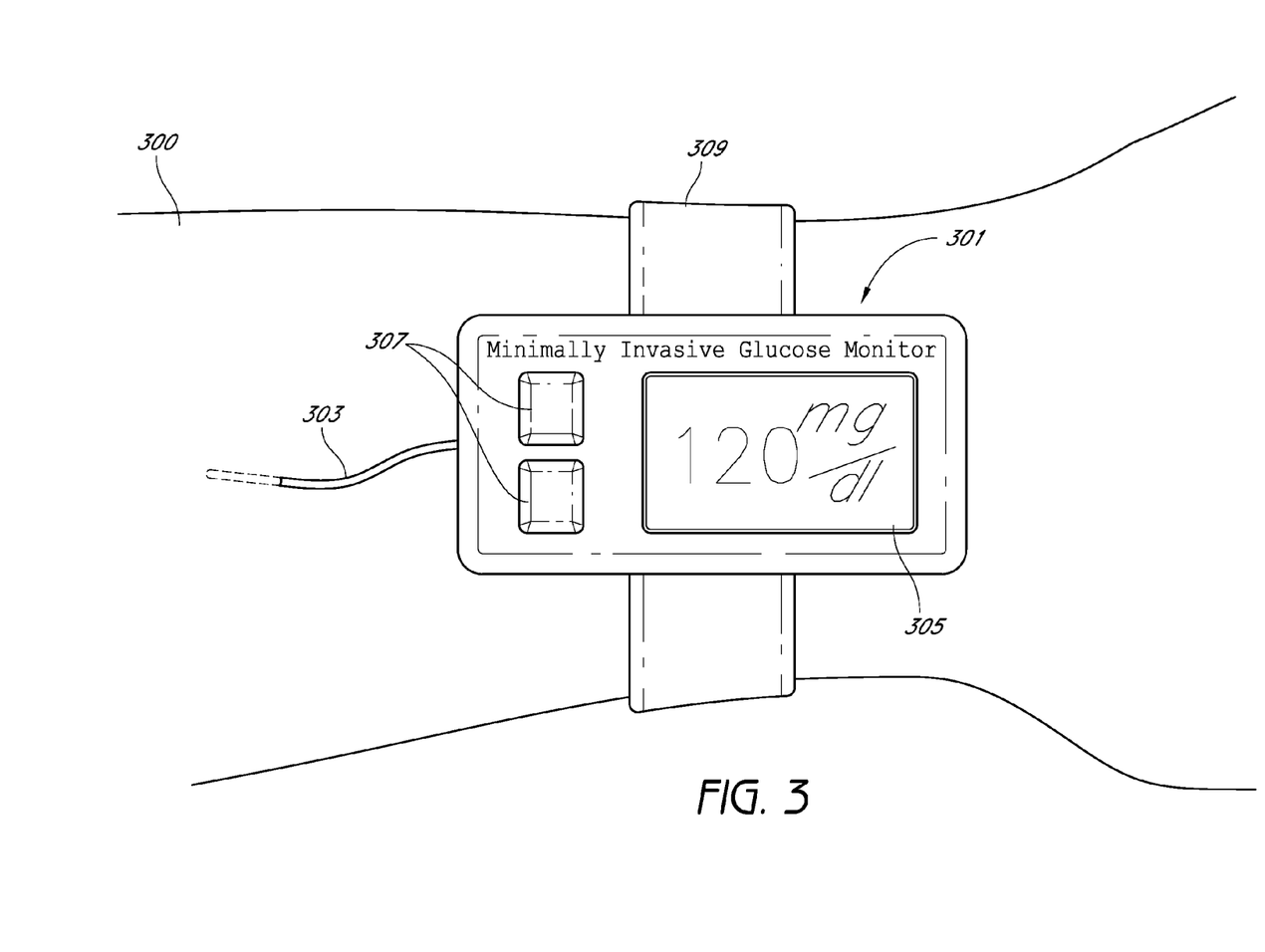
FIG. 3 illustrates a minimally invasive glucose monitor.

FIG. 3 illustrates an embodiment of a minimally invasive glucose monitor. As illustrated, a minimally invasive glucose monitor 301 is attached to a patient 300. The minimally invasive glucose monitor 301 includes a probe 303 which is inserted into the body, often just beneath the skin. The probe 303 measures glucose levels in the patient 300. The probe 303 communicates the measurements to the minimally invasive glucose monitor 301. In an embodiment, the probe 303 is attached to the monitor 301. In an embodiment, the probe is separate from the monitor 301. In an embodiment, the probe 303 communicates through a cable connection with the monitor 301. In an embodiment, the probe 303 communicates wirelessly with monitor 301. In an embodiment, the monitor 301 is attached to the patient 300 by attachment piece 309. In an embodiment, the monitor 301 includes a display 305. In an embodiment, the monitor includes one or more buttons 307.

In operation, the minimally invasive glucose monitor 301 continuously, nearly continuously, or intermittently (periodically or otherwise) measures blood glucose using probe 303. The probe detects glucose levels present in the body and communicates the glucose levels to the minimally invasive glucose monitor 301. The minimally invasive glucose monitor 301 calculates the patients glucose level based upon information acquired from probe 105. Examples of a minimally invasive glucose monitor and probe are described in U.S. Pat. No. 6,613,379, entitled "Implantable Analyte Sensor," issued to Ward et al., and U.S. Pat. No. 6,695,860, entitled "Transcutaneous Sensor Insertion Device," also issued to Ward et al, the entire contents of both of which are herein incorporated by reference.

Figure 4:
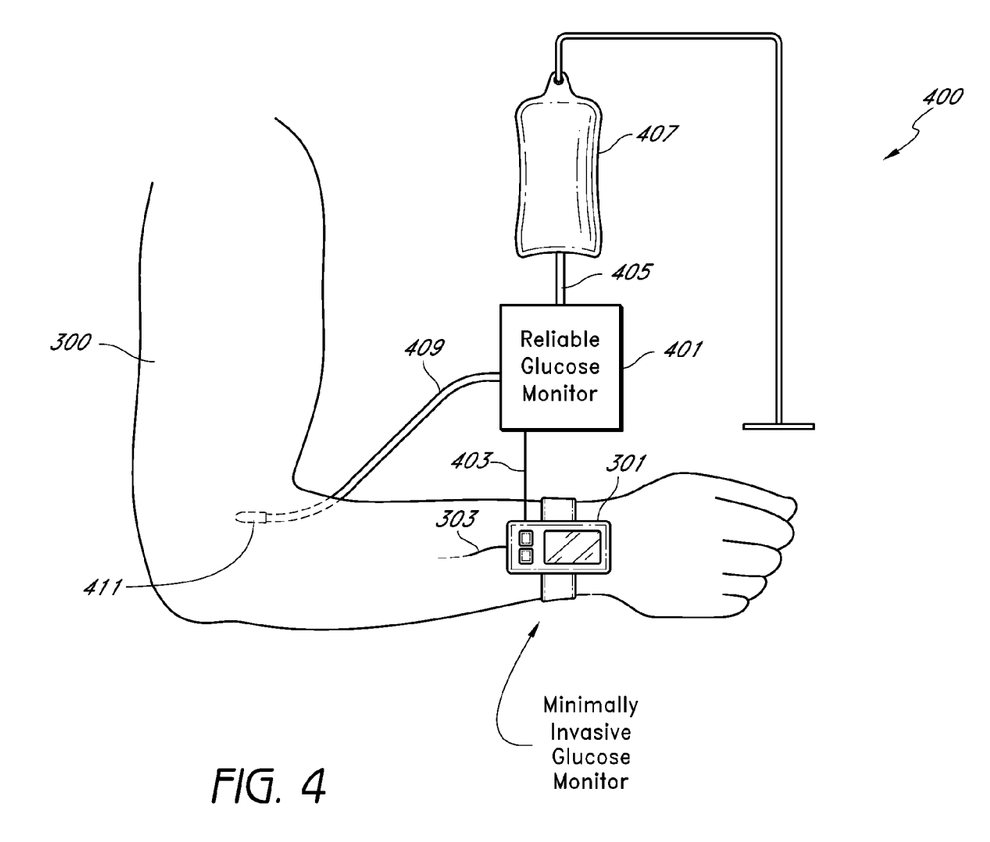
FIG. 4 illustrates a glucose calibration system.

FIG. 4 illustrates an embodiment of a glucose calibration system. For example, the glucose level of a patient 300 is measured by a minimally invasive glucose monitor 301. As described above, the minimally invasive glucose monitor 301 includes a probe 303 inserted into the patient 300 for measuring glucose levels. The glucose level of patient 300 is also measured by a reliable glucose monitor 401. The reliable glucose monitor 401 communicates data indicative of glucose levels in patient 300 to the minimally invasive glucose monitor 201. The minimally invasive glucose monitor 301 uses the communicated reliable data indicative of glucose levels in patient 300 to calibrate glucose information communicated by probe 303.

In an embodiment, the reliable glucose monitor 401 communicates with the minimally invasive glucose monitor 301 through a cable or a wireless connection. In an embodiment, the reliable glucose monitor 401 and the minimally invasive glucose monitor 301 communicate with a separate calibration unit either through a cable or wirelessly. In an embodiment, the minimally invasive glucose monitor 301 communicates with the reliable glucose monitor 401. In an embodiment, the minimally invasive glucose monitor 301 communicates a command to take a measurement to the reliable glucose monitor 401.

In an embodiment, the reliable glucose monitor 401 is operably connected to an IV line 409. The IV line 409 is operably connected to a catheter 411 which is inserted into a vein of the patient 300. The reliable glucose monitor 401 is also operably connected to an IV line 405 which is operably connected to an fluid bag 407. In operation, the reliable glucose monitor 401 intermittently draws blood from patient 300 through catheter 411 and IV line 409 and tests the blood for glucose levels. When the reliable glucose monitor 401 is not drawing blood from the patient 300, it supplies fluid to the patient 300 from fluid bag 407 and IV line 405 through IV line 409 and catheter 411. In an embodiment, the reliable glucose monitor 401 uses glucose test strips to measure glucose levels in the blood. In an embodiment, the reliable glucose monitor 401 uses chemicals analyses to test the glucose levels.

In an embodiment, the reliable glucose monitor 401 is programmed to take measurements at predetermined intervals. In an embodiment, the measurements are taken in intervals of about 5 minutes to about 12 hours. In an embodiment, the measurements are taken in intervals of about 5 minutes to about 10 minutes. In an embodiment, the measurements are taken in intervals of about 1 to about 2 hours. In an embodiment, the measurement intervals are dynamically determined based on calibration feedback as described below. In an embodiment, the minimally invasive glucose monitor 301, or another intermediary device communicate a take measurement command to the reliable glucose monitor. In an embodiment, the minimally invasive or intermediary device communicate a take measurement command in predetermined or dynamically determined intervals as described above.

Figure 4A:
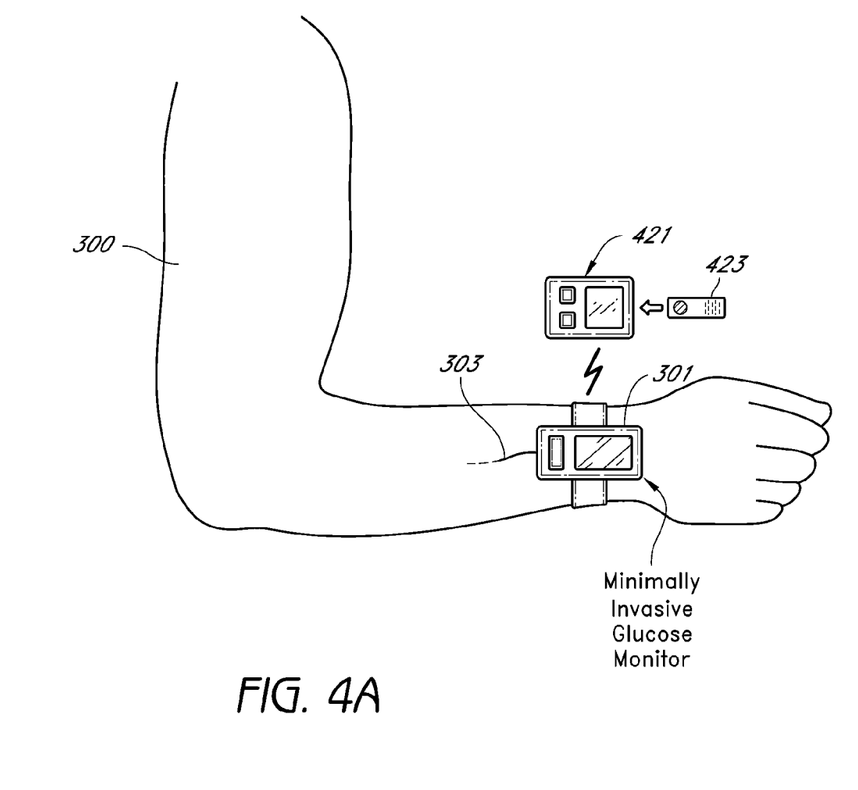
FIG. 4A illustrates another embodiment of a glucose calibration system.

FIG. 4A illustrates another embodiment of a glucose calibration system in which glucose test strips and a glucose test meter are used to measure glucose levels. A user uses the glucose test strips and glucose test meter to measure glucose levels. Once measured, the glucose test meter communicates the glucose levels to the minimally invasive glucose meter for calibration.

Figure 4B:
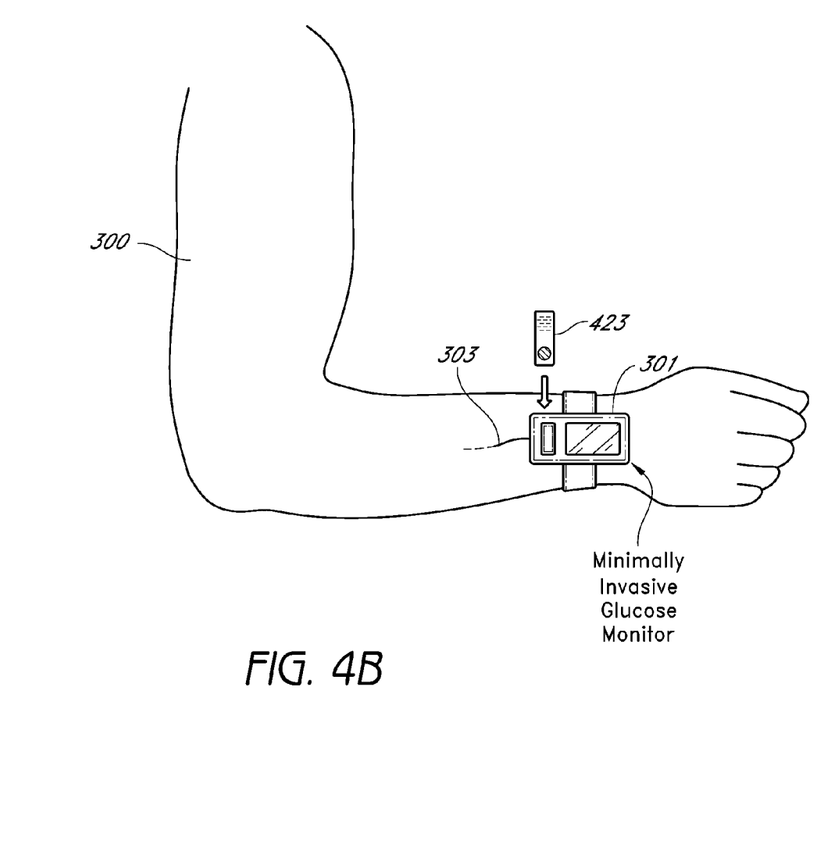
FIG. 4B illustrates yet another embodiment of a glucose calibration system.

FIG. 4B illustrates yet another embodiment of a glucose calibration system. In this embodiment, a glucose test meter is incorporated into the minimally invasive glucose monitor. A user uses the glucose test strips in conjunction with the minimally invasive glucose monitor to calibrate the minimally invasive glucose measurements. In an embodiment, the minimally invasive glucose monitor alerts a user that a reliable glucose measurement should be taken for calibration purposes.

Figure 5:
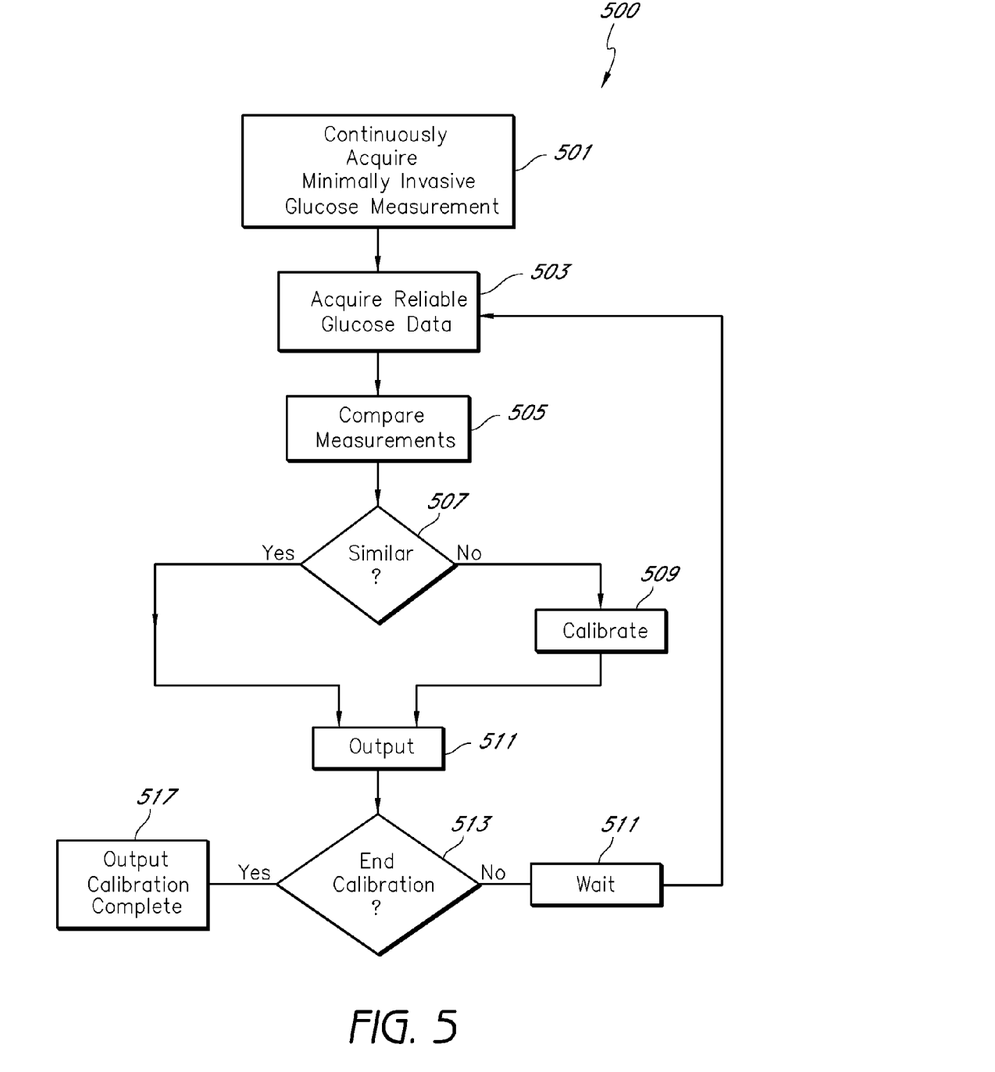
FIG. 5 illustrates a flow chart of an embodiment of a calibration system.

FIG. 5 illustrates a flow chart of an embodiment of a calibration system. The system begins by nearly continuously acquiring minimally invasive glucose measurements at block 501. The system then moves on to block 503 where the system acquires reliable glucose data. The system then moves on to block 505, where a calibration module compares the invasive blood glucose measurement to the acquired minimally invasive glucose measurement.

Once the measurements are compared, the system moves on to decision block 507, where the system looks to see if the measurements are the same or similar. Similar being defined herein as within a predetermined threshold. If the acquired minimally invasive measurement is the same or similar to the acquired reliable glucose data, then the system moves on to block 511 where the glucose reading is outputted, either to a display, a patient monitor, or to another device. If the minimally invasive measurement is not similar, or within a predetermined threshold, then the system moves on to block 509 where the minimally invasive measurements are calibrated. Once calibration is complete, the system moves on to block 511 where the glucose reading is outputted. The system then moves to block 513, where the system decides whether or not the calibration period is complete. If the calibration period is not complete, the system moves to block 515 where it waits a predetermined period of time. After the period of time is complete, the system returns to block 503 and repeats the calibration process. If at block 513, the calibration period is completed, then the system moves to block 517 where the system communicates a calibration complete signal.

In an embodiment, the determination of whether the calibration period is complete is based on an averaging of calibration periods required by other minimally invasive monitors. In an embodiment, the determination of whether the calibration period is compete is based on one or more comparisons of the reliable data and the minimally invasive measurement information. In one embodiment, the determination of whether the calibration period is complete is based on an averaging of calibration periods required by other minimally invasive monitors and one or more comparisons of the reliable data and the minimally invasive measurement information.

Figure 6:
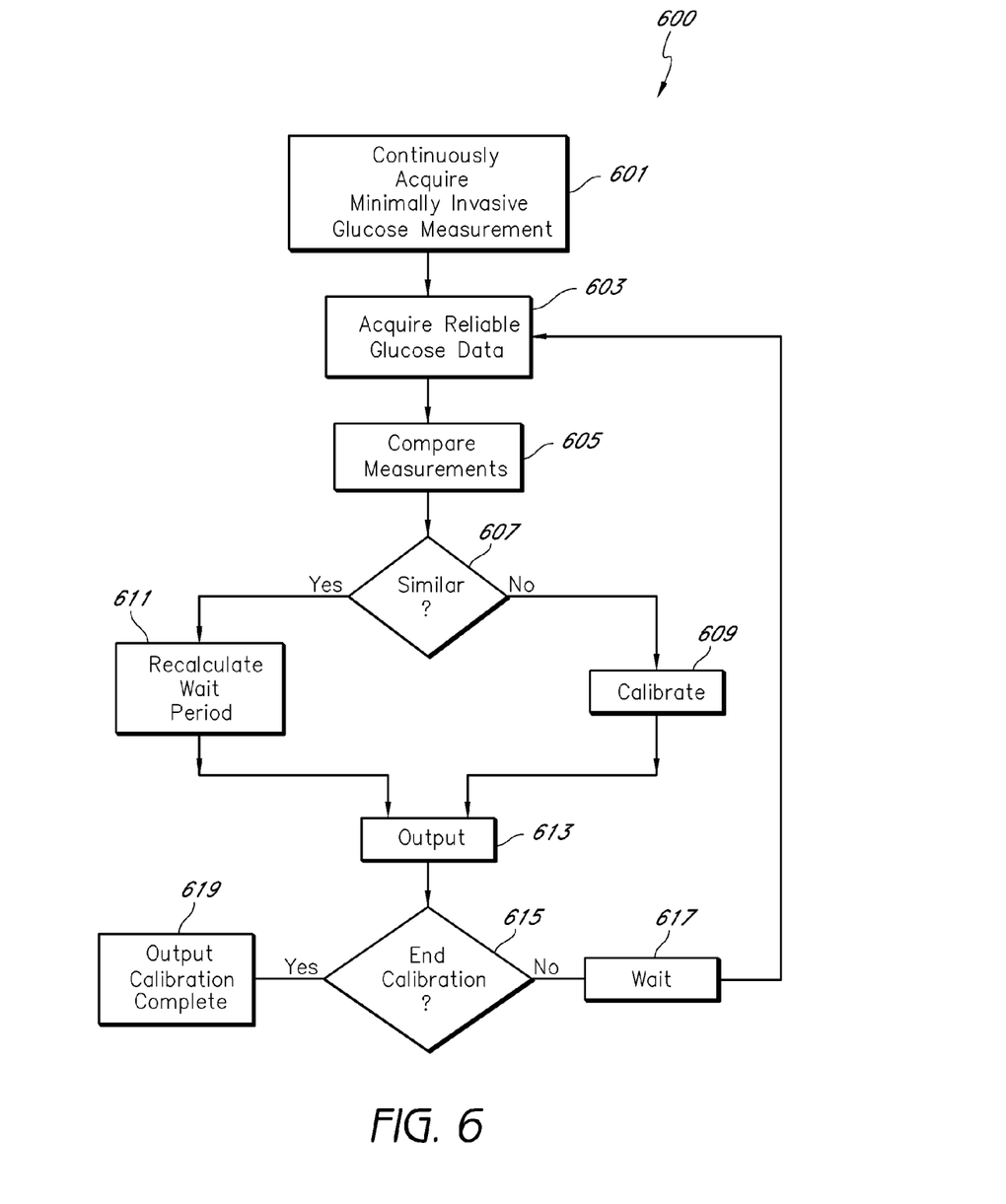
FIG. 6 illustrates a flow chart of another embodiment of a calibration system.

FIG. 6 illustrates a flow chart of another embodiment of a calibration system. The system begins by nearly continuously acquiring minimally invasive glucose measurements at block 601. The system then moves on to block 603 where the system acquires reliable glucose data. The system then moves on to block 605, where a calibration module compares the invasive blood glucose measurement to the acquired minimally invasive glucose measurement.

Once the measurements are compared, the system moves on to decision block 607, where the system looks to see if the measurements are similar. If the acquired minimally invasive measurement is the same or similar to the acquired reliable glucose data, then the system moves on to block 611 where the predetermined wait period of block 617 is recalculated. The recalculation can be based on the number of accurate readings made by the minimally invasive device and/or the accuracy level of the readings made by the minimally invasive device and/or any other parameter which is useful for determining the duration between calibration cycles. The system then moves on to block 613 where the glucose readings are outputted.

If the minimally invasive measurement is not similar, or within a predetermined threshold, then the system moves on to block 609 where the minimally invasive measurements are calibrated. The system then moves on to block 613 where the glucose readings are outputted. Once calibration is complete, the system moves on to block 615, where the system decides whether or not the calibration period is complete. If the calibration period is not complete, the system moves to block 617 where it waits the predetermined period of time, either as initially set or as dynamically recalculated at block 611. After the period of time is complete, the system returns to block 503 and repeats the calibration process. If at block 615, the calibration period is completed, then the system moves to block 619 where the system communicates a calibration complete signal.

Although the foregoing invention has been described in terms of certain preferred embodiments, other embodiments will be apparent to those of ordinary skill in the art from the disclosure herein. For example, an invasive blood pressure monitor can be used to calibrate a non-invasive blood pressure monitor. In addition, various types of physiological monitors can be used to calibrate various other types of physiological monitors. For example, a minimally invasive physiological monitor can be used to calibrate a non-invasive physiological monitor. Additionally, other combinations, omissions, substitutions and modifications will be apparent to the skilled artisan in view of the disclosure herein. It is contemplated that various aspects and features of the invention described can be practiced separately, combined together, or substituted for one another, and that a variety of combination and subcombinations of the features and aspects can be made and still fall within the scope of the invention. Furthermore, the systems described above need not include all of the modules and functions described in the preferred embodiments. Accordingly, the present invention is not intended to be limited by the recitation of the preferred embodiments, but is to be defined by reference to the appended claims.

What is claimed is:

1. A calibration system for calibrating a physiological measurement monitor comprising:
    a first physiological monitor configured to continuously measure a physiological analyte of a patient;
    a calibration module comprising:
        a first communication port configured to receive measured physiological data from the first physiological monitor; and
        a second communication port communicating with a non-continuous, invasive physiological measurement device and receiving reliable data indicative of one or more physiological parameters from the non-continuous, invasive physiological measurement device, the non-continuous, invasive physiological measurement device configured to automatically extract blood from a patient intravenously and test the blood automatically to determine a reliable indication of the physiological analyte of the patient, the calibration module configured to automatically communicate commands to the invasive physiological measurement device to take measurements at dynamic intervals based on calibration feedback; and
    wherein the calibration module is configured to calibrate the first physiological monitor using the information received over the first and second communication ports.

2. The calibration system of claim 1, wherein the first physiological monitor comprises a minimally invasive physiological measurement device.

3. The calibration system of claim 1, wherein the first physiological monitor comprises a non invasive physiological measurement device.

4. The calibration system of claim 1, further comprising one or more signal outputs.

5. The calibration system of claim 4, wherein at least one of the one or more signal outputs comprises a display output.

6. The calibration system of claim 4, wherein at least one of the one or more signal outputs comprises a waveform output.

7. The calibration system of claim 6, wherein the waveform output comprises a scaled waveform.

* * * * *